(12) United States Patent
Shipeng et al.

(10) Patent No.: US 6,438,203 B1
(45) Date of Patent: Aug. 20, 2002

(54) WHOLE-BODY RADIOTHERAPY DEVICE WITH MULTIPLE RADIOACTIVE SOURCES

(75) Inventors: Song Shipeng; Liu Guangwu, both of Shenzhen (CN)

(73) Assignee: Shen Zhen Hyper Technology Incorporation, Guangdong Province (CN)

( * ) Notice: Subject to any disclaimer, the term of this patent is extended or adjusted under 35 U.S.C. 154(b) by 0 days.

(21) Appl. No.: 09/564,517

(22) Filed: May 4, 2000

(30) Foreign Application Priority Data

May 31, 1999  (CN) .......................................... 99108217

(51) Int. Cl.[7] ................................................ A61N 5/10
(52) U.S. Cl. ....................................................... 378/65
(58) Field of Search ........................................... 378/65

(56) References Cited

U.S. PATENT DOCUMENTS 5,894,503 A  *  4/1999  Shepherd et al. ............. 378/65

* cited by examiner

*Primary Examiner*—Craig E. Church
(74) *Attorney, Agent, or Firm*—Westman, Champlin & Kelly, P.A.

(57) ABSTRACT

The present invention discloses a whole-body radiotherapy device with multiple radioactive sources, comprising rotary fixing frame, source body and collimator body whose rotating axis is parallel to the longitudinal axis of the treatment couch. Multiple radioactive sources and their beam channel are distributed in said source body, land the beam from said radioactive sources focus on the common focus point through said beam channel. The collimators are located in the collimator body, and they have the same distribution pattern as the radioactive sources. The source body and the collimator body are fixed on the rotary fixing frame and can be made to rotate around the rotating axis. In the radial sectional planes, radioactive sources and their beam channels are located within a fan shaped area whose included angle is less than 90°. With the guarantee of retaining enough treatment space for the whole body, the source-focus-distance is greatly reduced. As a result, the total radiation activity and the production cost of the sources are greatly reduced, the utility efficiency of the radioactive sources is improved, the volume size, the weight and the production cost of the device are reduced.

15 Claims, 3 Drawing Sheets

WHOLE-BODY RADIOTHERAPY DEVICE WITH MULTIPLE RADIOACTIVE SOURCES

FIELD OF THE INVENTION

The present invention relates to radiotherapy devices, and more particularly to a rotary whole-body radiotherapy device with multiple radioactive sources.

BACKGROUND OF THE INVENTION

Rotary whole-body radiotherapy device with multiple radioactive sources works on the principle of focusing while rotating. The multiple radioactive sources installed in the rotary source body are made to rotate in a family of coaxial conical planes, and directing at the common focus point coincident with the common vertex of the conical planes. As a result, the lesion tissue located at the common focus point is killed, while the healthy tissue are spared by receiving only instant and harmless radiation. In the view of nuclear physics, the dose of the radioactive source at the focus point is in reverse proportion to the square of the distance between the radioactive source and the focus point. On the one hand, the distance from the center of the radioactive source to the focus point should be as short as possible, and on the other hand, to implement rotary radiation to disease site located at any place of the patient, there should be enough space from the exit of the collimator to the body surface of the patient. In the prior art, the radioactive sources are uniformly distributed on the rotary cylindrical source body which rotates in full angle range of 360°. Such an arrangement is known from CN Patent No. 96213589.5, which discloses a rotary whole-body radiotherapy device with a source body of hollow cylindrical shape. Take the plane which passes the focus point and perpendicular to the center line of the hollow cylinder as the datum plane, the radioactive sources are arranged in several groups on the cylindrical plane from latitudes 3° to 48° relative to the reference plane. On the surface plane of the cylindrical source body, the groups of channels are distributed uniformly along the circumference as viewed from the axial direction, they can be either spaced equidistantly in parallel, or ascending one line by each group. The collimators and the shielding rods are distributed in the same pattern as the radioactive sources, and as a result, beam channels are formed. Since the radioactive sources and the collimators are distributed within a full angle range of 360° along the circumference, the internal radius of the hollow cylinder should be no less than the distance from the exit of the collimators to the focus point is equal to. In order to implement radiation to the disease site at any place of the patient, said internal radius should be greater than the width of a human body, i.e., the distance from the exit of the collimators to the focus point should be greater than 48 centimeters. Therefore, in the prior art device, the radioactive sources have high total radiation activity, expensive production cost, low utility efficiency, and require critical shielding. As a result, the device is bulky in volume, heavy in weight, and high in production cost.

SUMMARY OF THE INVENTION

The primary objective of the present invention is to provide a whole-body radiotherapy device with multiple radioactive sources renovated in configuration, so as to shorten the distance (referred to as source-focus-distance) from the radioactive sources to the focus point, and consequently improve the utility efficiency of the radioactive sources, reduce the volume and weight of the device.

In accordance with the present invention, there is provided a whole-body radiotherapy device with multiple radioactive sources, comprising rotary fixing frame, source body and collimator body whose rotating axis is parallel to the longitudinal axis of the treatment couch. Multiple radioactive sources and their. beam channel are distributed in said source body, and the beam from said radioactive sources focus on the common focus point through said beam channel. The collimators are located in the collimator body, and they have the same distribution pattern as the radioactive sources. The source body and the collimator body are fixed on the rotary fixing frame and can be made to rotate around the rotating axis. Taking the plane which passes the common focus point and perpendicular to the rotating axis as a datum plane, said datum plane is made to rotate around the line which passes the common focus point and perpendicular to the rotating axis. As a result, a family of planes are formed which are defined as radial sectional planes. In said radial sectional planes, radioactive sources and their beam channels are located within a fan shaped area whose included angle is less than 90°.

Since the radioactive sources and their beam channels are located within a fan shaped area whose included angle is less than 90°, instead of distributing in full angle range of 360° in said radial section planes, the radioactive sources and their beam channels can be limited to the region of a very narrow fan shape. Making the inner rotary radius of the collimator body longer than half width of the human body, the rotary radiotherapy at any place of the human body can be implemented by positioning the disease site at the focus point, and selecting the incidence angle and rotary range of the beam accordingly, instead of rotating in full angle range of 360°. Therefore, the contradictory between the demands of a large treatment space and a short source-focus-distance is successfully solved. With the guarantee of, retaining enough treatment space for the whole body, the source-focus-distance is greatly reduced. As a result, the total radiation activity and the production cost of the sources are greatly reduced, the utility efficiency of the radioactive sources is improved, the volume size, the weight and the production cost of the device are reduced. Consequently, significant economic effect and social effect are achieved.

DETAILED DESCRIPTION OF THE PREFERRED EMBODIMENT

Figure 1:
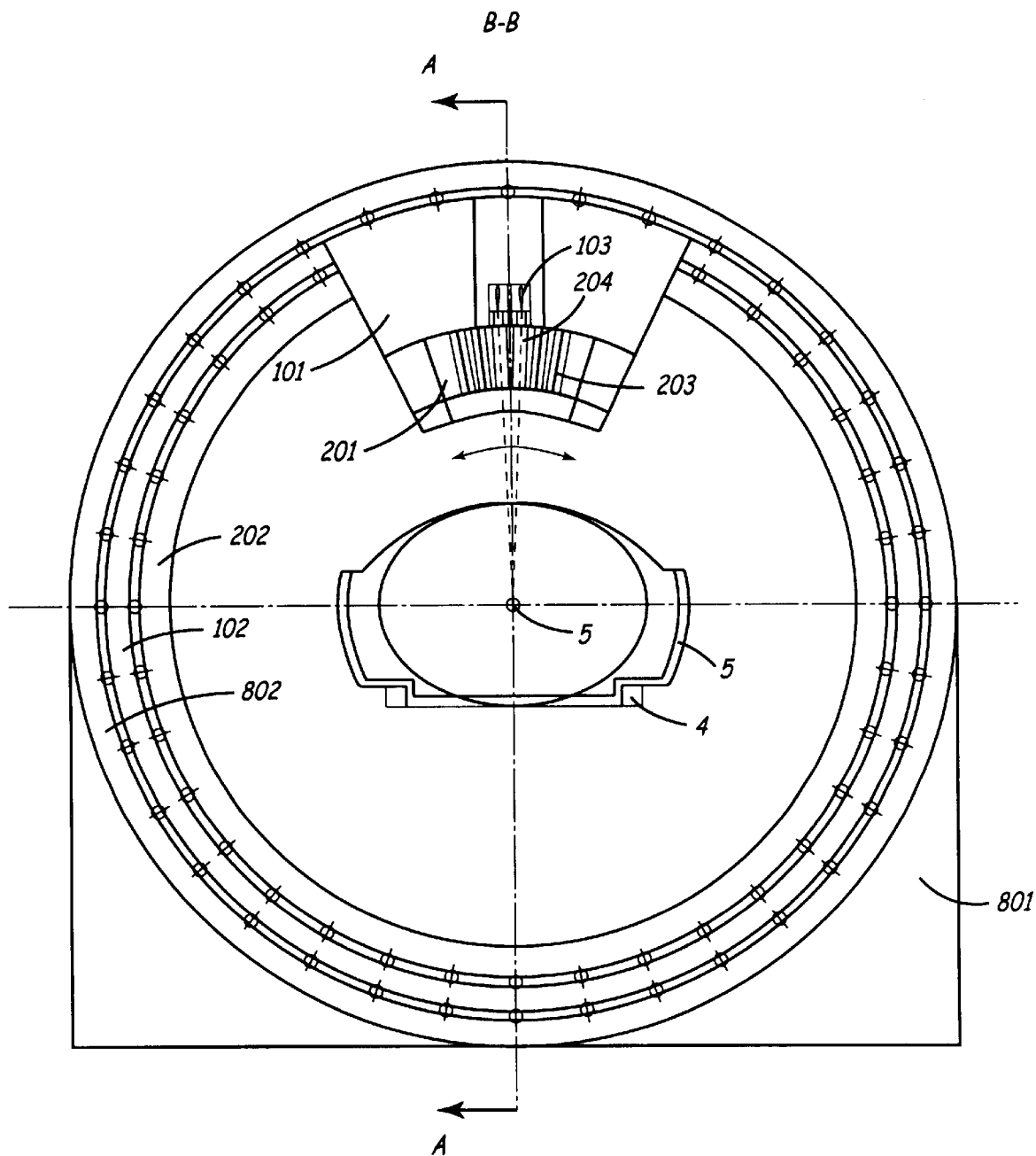
FIG. 1 is a radial (B—B) sectional graph showing one preferred embodiment of the whole-body radiotherapy device with multiple radioactive sources in accordance with the present invention.
Figure 6:
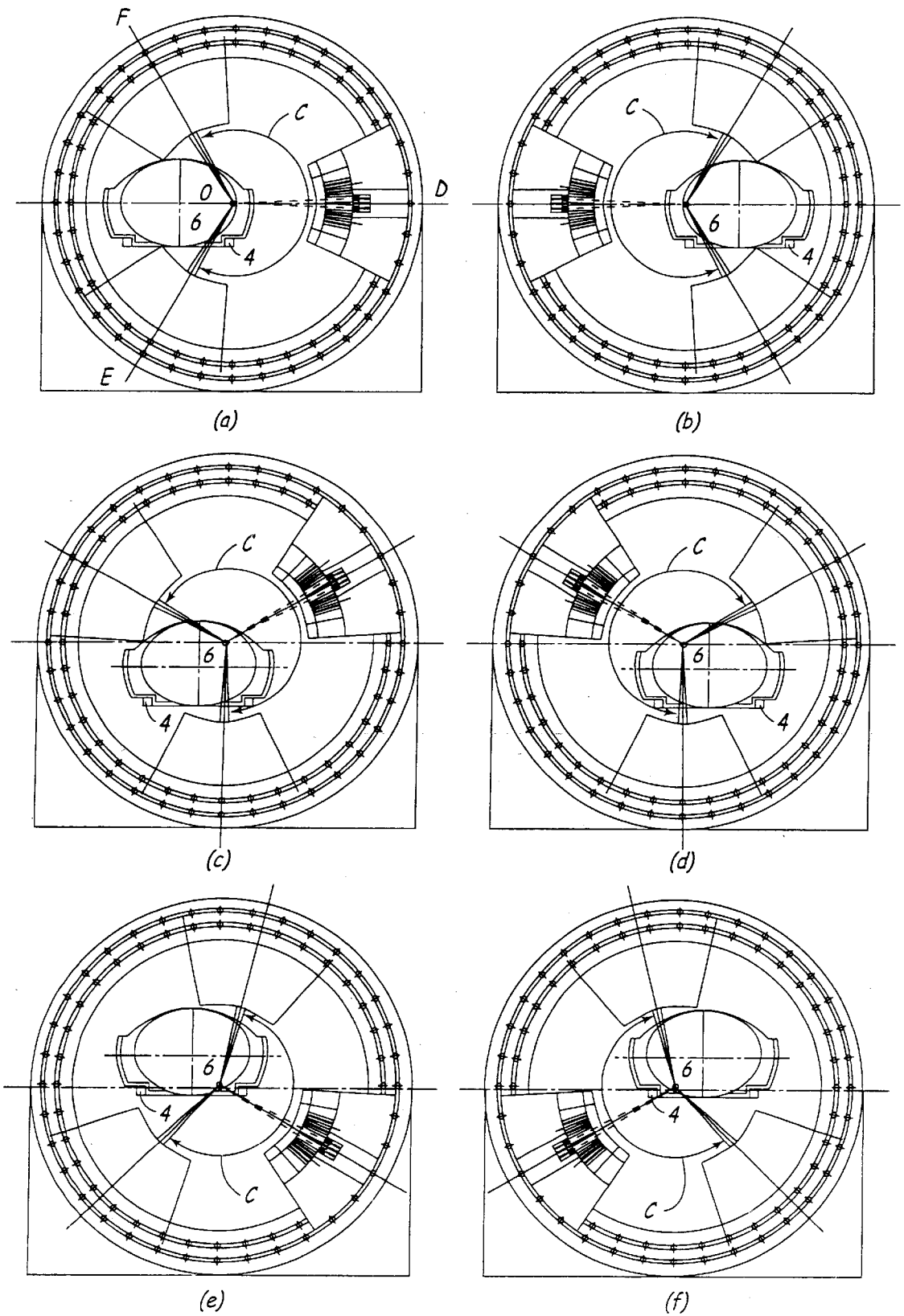
FIGS. 6(a)–(f) are graphs showing examples of radiation with different incident angles and rotary range according to different positions of the disease site.

Referring to FIG. 1, in one preferred embodiment of the present invention, the whole-body radiotherapy device with multiple radioactive sources comprises source body 101, rotary source body fixing ring 102 which is fixed with said source body 101, collimator body 201, rotary collimator body fixing ring 202 which is fixed with said collimator body 201, support frame 801, and rotary support ring 802 which is fixed with said support frame 801. Wherein, multiple rolling bearings are installed between said rotary source body fixing ring 102 and said rotary support ring 802. As a result, said rotary source body fixing ring 102 are axially fixed with but can rotate relative to said rotary support ring 802. Similarly, multiple rolling bearings are installed between the rotary collimator body fixing ring 202 and the rotary source body fixing ring 102. The source body fixing ring 102 and the collimator body fixing ring 202 are driven to rotate by two servo motors respectively, the source body 101 carried by the source body fixing ring 102 and the collimator body 201 carried by the collimator body fixing ring 202 are consequently driven to rotate. Thus, the relative position between the source body 101 and the collimator body 201 can be adjusted, and the source body 101 can be made to stay at any position, so that the initial and final incident angles of the source body 101 with relative to the common focus point 6 can be adjusted. As seen from the example shown in FIG. 6(a), the initial incident angle is ∠DOF, the final incident angle a is ∠DOE, and the rotating angle range is C. In the source body 101, multiple radioactive sources 103 and their beam channels are distributed. Beam from said radioactive sources 103 pass through said beam channels and focus on the common focus point 6 located on the rotating axis 7. In the radial sectional planes, radioactive sources and their beam channels are located within a fan shaped area whose included angle is less than 90°. Said included angle is further preferred to be less than 30°. While in this embodiment, the two lines of radioactive sources are spaced by 4.5°.

Figure 2:
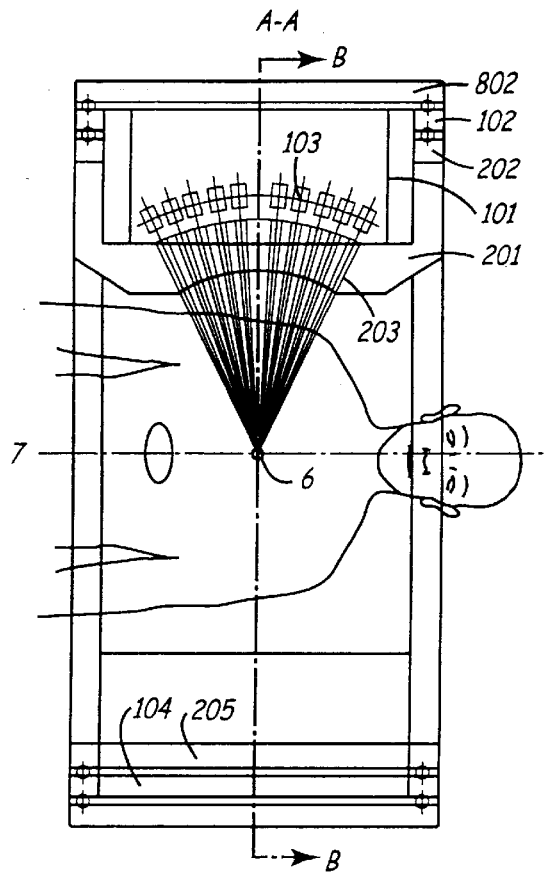
FIG. 2 is the axial (A—A) sectional graph of the whole-body radiotherapy device with multiple radioactive sources as defined in FIG. 1.

In the axial sectional plane, radioactive sources and their beam channels are located within a fan shaped area whose included angle is less than 60°. Referring to FIG. 2, in this embodiment of the present invention, in the axial sectional plane, the radioactive sources and their beam channels are distributed in a fan shaped pattern with equal source-focus-distance. They are distributed within two regions whose included angles are from −25° to 5° and from 5° to 25° respectively. And the radiation strength of each radioactive source 103 at the common focus point 6 is equal. With this distribution pattern, the shape of the radiation field at the focus point can be more approximately to a circle shape, and in the same time, the, penumbra of the radiation field at the focus point in the radial plane can be reduced. The rotating axis 7 passes the common focus point 6 and parallel to the longitudinal axis of the treatment couch. In order to keep balance while rotating, a source body counterweight 104 is installed in the rotary source body fixing ring 102, and a collimator body counterweight 206 is installed in the rotary collimator body fixing ring 202.

Figure 3:
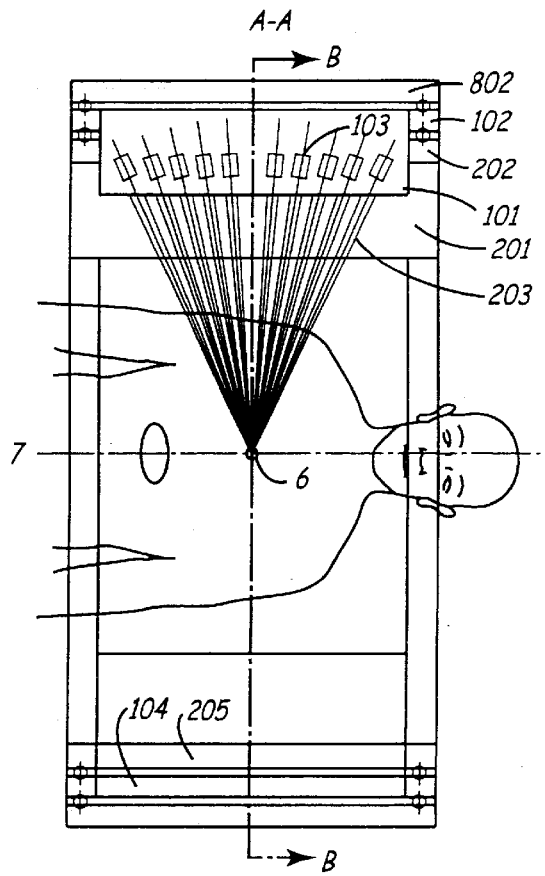
FIG. 3 is the axial (A—A) sectional graph showing another preferred embodiment of the whole-body radiotherapy device with multiple radioactive sources in accordance with the present invention.

Referring to FIG. 3, in another preferred embodiment of the present invention, in the axial sectional plane, the radioactive sources and their beam channels are distributed in a triangular pattern with non-equal source-focus-distance. With this distribution pattern, the radiation strength of radioactive sources 103 may not be equal with each other at the common focus point 6.

Figure 4:
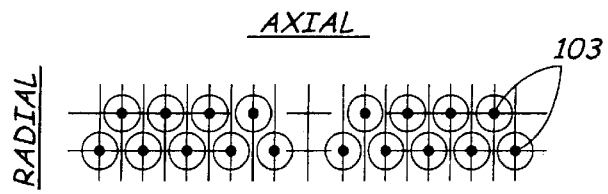
FIG. 4 is the graph showing the distribution of the radioactive sources in the source body of the whole-body radiotherapy device with multiple radioactive sources in accordance with the present invention.

Referring to FIG. 4, the radioactive sources 103 are distributed in two adjacent axial sectional planes, and stagger distributed in different radial sectional planes. So that, beam of each radioactive source forms non overlapped conical planes with others while rotating.

Figure 5:
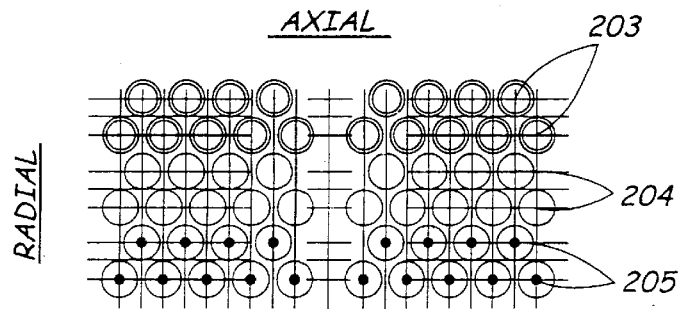
FIG. 5 is the graph showing the distribution of the collimators and the shielding rods in the collimator body of the whole-body radiotherapy device with multiple radioactive sources in accordance with the present invention.

Referring to FIG. 5, two sets 203, 205 of collimators with different diameter and one set of shielding rods 204 are installed in the collimator body 201. Each set has the same distribution pattern as radioactive sources 103. By adjusting the longitude position (±9°) of the collimator body 201 with relative to the source body 101, the radioactive sources 103 located in the source body 101 can be registered with one set of collimators or shielding rod. Then the source body 101 and the collimator body 201 are made to rotate synchronously. As a result, we can select collimators of different. diameters or shut the beam automatically as desired within the rotating angle range, so as to spare sensitive organs of the patient.

As seen from FIGS. 6(a)–(f) the lesion is located at the left, the right, the upper left, the upper right, the lower left and the lower right of the patient respectively. In the plane which passes the focus point 6 and perpendicular to the rotating axis 7, the distance from the internal edge of the collimator body fixing ring 202 to the common focus point 6 is less than the full width but more than the half-width of the human body, e.g., 28 cm. The rotating angle range C of the source body and the collimator body is not 360°, but is calculated based on the particular position of the lesion to avoid interference with the human body and treatment couch. Alternately, the rotating angle range C can be decided by the doctor according to the incident depth of the beam. In treatment, by moving the treatment couch 4, the disease site is positioned at the focus point 6. Then the radiation is implemented within the rotating angle range selected according to the treatment plan. If one set of collimators is registered with the radioactive sources, the beam from the radioactive sources will reach the common focus point through the collimators. If a set of shielding rods is made to register with the radioactive sources, the beam will be blocked. The changing between the collimators and the shielding rod is realized by two servo motors which respectively drive the rotary source body fixing ring carried with the source body and the rotary collimator body fixing ring carried with the collimators. And then the source body and the collimator body are made to rotate synchronously. As a result, we can open or shut the beam automatically as desired within the rotating angle range, so as to spare sensitive tissues of the patient.

What is claimed is:

1. A whole-body radiotherapy device with multiple radioactive sources, comprising, a rotary fixing frame, a source body and a collimator body having a rotating axis which is parallel to a longitudinal axis of a treatment couch;

said source body having multiple radioactive sources and beam channels located therein, and wherein beams from said radioactive sources focus on a common focus point through said beam channels;

said collimator body having collimators located therein, and said collimators have the same distribution pattern as the radioactive sources, said source body and said collimator body are fixed on said rotary fixing frame and can rotate around the rotating axis;

in radial sectional planes, said radioactive sources and their beam channels are located within a fan shaped area whose included angle is less than 90°;

said radioactive sources are distributed in two adjacent axial sectional planes which are spaced by 4°–5°, and stagger distributed in different radial sectional planes;

said collimator body having an internal radius which is less than a full width of a human body, but more than half-width of a human body.

2. The device as defined in claim 1 wherein, in the axial sectional planes, the radioactive sources and their beam channels are distributed in a fan shaped pattern with equal source focus-distance.

3. The device as defined in claim 1 wherein, in the axial sectional planes, the radioactive sources and their beam channels are distributed in a triangular pattern with non-equal source focus-distance.

4. The device as defined in claim 1 wherein, an initial and a final incident angles of the beams from the source body relative to the common focus point are adjustable.

5. The device as defined in claim 1 further comprises:
   a rotary support ring which is fixed with said fixing frame;
   a rotary source body fixing ring which is fixed with said source body; and
   wherein said rotary source body fixing ring is axially fixed with and can rotate relative to said rotary support ring.

6. The device as defined in claim 1 further comprises:
   a rotary collimator body fixing ring which is fixed with said collimator body; and
   wherein said rotary collimator body fixing ring is axially fixed with and can rotate relative to said rotary source body fixing ring.

7. The device as defined in claim 1 wherein, said collimators are divided into several sets, each set of collimators have the same diameter, and have the same distribution pattern as said radioactive sources.

8. The device as defined in claim 1, said collimator body having a set of shielding rods located therein, said shielding rods having the same distribution pattern as said radioactive sources.

9. The device as defined in claim 1 wherein, said half-width of the human body is about 28 cm.

10. The device as defined in claim 1 wherein, in the radial sectional planes, said radioactive sources and their beam channels are located within a fan shaped area whose included angle is less than 30°.

11. The device as defined in claim 10 wherein an initial and a final incident angles of the beams from the source body relative to the common focus point can be adjusted.

12. The device as defined in claim 10 further comprises:
    a rotary support ring which is fixed with said fixing fame;
    a rotary source body fixing ring which is fixed with said source body; and
    wherein said rotary source body fixing ring is axially fixed with and can rotate relative to said rotary support ring.

13. The device as defined in claim 10 further comprises:
    a rotary collimator body fixing ring which is fixed with said collimator body; and
    wherein said rotary collimator body fixing ring is axially fixed with and can rotate relative to said rotary source body fixing ring.

14. The device as defined in claim 10 wherein, said collimators are divided into several sets, each set of collimators have the same diameter, and have the same distribution pattern as said radioactive sources.

15. The device as defined in claim 10, said collimator body having a set of shielding rods located therein, said shielding rods having the same distribution pattern as said radioactive sources.

* * * * *